United States Patent [19]
Schock et al.

[11] Patent Number: 5,490,820
[45] Date of Patent: Feb. 13, 1996

[54] ACTIVE COMPRESSION/DECOMPRESSION CARDIAC ASSIST/SUPPORT DEVICE AND METHOD

[75] Inventors: Robert B. Schock, Sparta; Victoria Hunsicker-Sanko, Montclair, both of N.J.

[73] Assignee: Datascope Investment Corp., Montvale, N.J.

[21] Appl. No.: 31,195

[22] Filed: Mar. 12, 1993

[51] Int. Cl.$^6$ .................................................. A61H 31/00
[52] U.S. Cl. .................................. 601/41; 601/1; 601/44; 601/151
[58] Field of Search ........................ 128/24 R, 28, 128/30, 30.2, 50, 53, 60, 61, 64, 874, DIG. 20; 602/13, 19; 601/1, 11, 15, 41, 105, 106, 148, 149, 150, 151, 152, 43, 44

[56] References Cited

U.S. PATENT DOCUMENTS

| | | | |
|---|---|---|---|
| 2,071,215 | 2/1937 | Petersen | 601/106 |
| 2,529,258 | 11/1950 | Lobo | 601/44 |
| 2,869,537 | 1/1959 | Chu | 601/44 |
| 3,219,031 | 11/1965 | Rentsch, Jr. | |
| 3,509,899 | 5/1970 | Hewson | |
| 3,896,797 | 7/1975 | Bucur | |
| 4,248,215 | 2/1981 | Bleakley | 128/60 |
| 4,397,306 | 8/1983 | Weisfeldt et al. | |
| 4,424,806 | 1/1984 | Newman et al. | |
| 4,753,226 | 6/1988 | Zhing et al. | 601/150 |
| 4,862,879 | 9/1989 | Coombs | 602/13 |
| 4,928,674 | 5/1990 | Halperin et al. | |
| 4,971,042 | 11/1990 | Lerman | 128/30 |
| 5,222,478 | 6/1993 | Scarberry et al. | |

FOREIGN PATENT DOCUMENTS

| | | | |
|---|---|---|---|
| 1225889 | 8/1987 | Canada | 128/28 |
| 0509773 | 10/1992 | European Pat. Off. | |
| 2624008 | 6/1989 | France | 128/28 |
| 1560204 | 4/1990 | U.S.S.R. | 128/30 |

OTHER PUBLICATIONS

Lueptow, Richard M. et al., "Circulatory Model Studies of External Cardiac Assist by Counterpulsation," Cardiovascular Research, vol. XV, No. 8, Aug. 1981, pp. 443–455.

Chandra, Nisha, et al., "Augmentation of Carotid Flow During Cardiopulmonary Resuscitation by Ventilation at High Airway Pressure Simultaneous with Chest Compression," Johns Hopkins Hospital, 1981.

Lueptow, R. M. et al., "Study of Four Modes of Counterpulsative External Cardiac Assist," Trans. Am. Soc. Artif. Intern. Organs, vol. XXVII, 1981, pp. 576–581.

Weisfeldt, Myron L. et al., "Physiology of Cardiopulmonary Resuscitation," Ann. Rev. Med., vol. 32, 1981, pp. 435–442.

Koehler, Raymond C. et al., "Augmentation of Cerebral Perfusion by Simultaneous Chest Compression and Lung (List continued on next page.)

*Primary Examiner*—Richard J. Apley
*Assistant Examiner*—Jeanne M. Clark
*Attorney, Agent, or Firm*—Fitzpatrick, Cella, Harper & Scinto

[57] ABSTRACT

An active compression/decompression CPR device capable of providing both complete cardiopulmonary support and cardiopulmonary assistance includes two or more thoracic compressors, preferably inflatable bladders, positioned so that the chest can first be flattened and compressed, increasing the pressure in the chest, and then circularized and decompressed, decreasing the pressure in the chest. When inflatable bladders are used, they can be surrounded with a rigidifying vest which resists outward bladder expansion. Compression and decompression can be performed along with abdominal compression, and the device is capable of shifting between support and assist modes when the patient's condition so requires. Also described is a method of compressing and then decompressing a patient's thorax by applying anterior and/or posterior pressure to the thorax, so as to compress the thorax and increase pressure therein, relieving that pressure, and then applying lateral pressure to the thorax to decompress and relieve pressure in the thorax, and then relieving the lateral pressure.

45 Claims, 6 Drawing Sheets

OTHER PUBLICATIONS

Inflation with Abdominal Binding After Cardiac Arrest in Dogs," Circulation, vol. 67, No. 2, Feb. 1983, pp. 266–275.

Pinsky, Michael R. et al., "Augmentation of Cardiac Function by Elevation of Intrathoracic Pressure," *J. Appl. Physiol., vol. 54, No. 54, 1983, pp. 950–955.*

Beyar, Rafael, et al., "Cardiopulmonary Resuscitation by Intrathoracic Pressure Variations: In Vivo Studies and Computer Simulation," Vascular Diseases, Feb. 1984, pp. 71–78.

Maier, George W. et al., "The Physiology of External Cardiac Massage: High Impulse Cardiopulmonary Resuscitation," Circulation, vol. 70, No. 1, Jul. 1984, pp. 86–101.

Criley, J. Michael et al., "Cardiopulmonary Resuscitation Research 1960–1984: Discovering and Advances," Annals of Emergency Medicine, vol. 13, No. 9, Sep. 1984, pp. 756–758.

Niemann, James T. et al., "Circulatory Support During Cardiac Arrest Using a Pneumatic Vest and Abdominal Binder with Simultaneous High-Pressure Airway Inflation," Annals of Emergency Medicine, vol. 13, No. 9, Sep. 1984, pp. 767–769.

Luce, John M. et al., "Regional Blood Flow During Cardiopulmonary Resuscitation in Dogs," Critical Care Medicine, vol. 12, No. 10, Oct. 1984, pp. 874–948.

Sanders, Arthur B. et al., "The Physiology of Cardiopulmonary Resuscitation," JAMA, vol. 252, No. 23, Dec. 1984, pp. 3283–3286.

Beyar, R. et al., "Noninvasive Cardiac Assist by Extension of Phased Compression Cardiopulmonary Resuscitation," *Trans. Am. Soc. Artif. Intern. Organs, vol. XXX, 1984, pp. 103–107.*

Cummins, Richard O. et al., "Prehospital Cardiopulmonary Resuscitation: Is It Effective?" JAMA, vol. 253, No. 16, Apr. 15, pp. 2408–2412.

Soroff, Harry S. et al., "Current Status of External Counterpulsation," Critical Care Clinics, vol. 2, No. 2, Apr. 1986, pp. 277–295.

Weisfeldt, Myron L. et al., "Cardiopulmonary Resuscitation: Beyond Cardiac Massage," Circulation, vol. 74, No. 3, Sep. 1986, pp. 443–448.

Criley, John Michael et al., "Modifications of Cardiopulmonary Resuscitation Based on the Cough," Circulation, vol. 74, Suppl. IV, Dec. 1986, pp. IV-42–IV-50.

Ewy, Gordon A., "Alternative Approaches to External Chest Compression," Circulation, vol. 74, Suppl. IV, Dec. 1986, pp. IV-98–IV-101.

Halperin, Henry R. et al., "Vest Inflation Without Simultaneous Ventilation During Cardiac Arrest in Dogs: Improved Survival from Prolonged Cardiopulmonary Resuscitation," Circulation, vol. 74, No. 6, Dec. 1886, pp. 1407–1415.

Paraskos, John A., "External Compression Without Adjuncts," Circulation, vol. 74, Suppl. IV, Dec. 1986, pp. IV-33–IV-36.

Kern, Karl B. et al., "Comparison of Mechanical Techniques of Cardiopulmonary Resuscitation," Am. J. Emergency Medicine, vol. 5, No. 3, May 1987, pp. 190–195.

Lin, Ching-Kow et al., "Optimization of Coronary Blood Flow During Cardiopulmonary Resuscitation (CPR)," IEEE Trans. Biomedical Engineering, vol. BME-34, No. 6, Jun. 1987, pp. 473–481.

Halperin, H. R. et al., "Programmable Pneumatic Generator for Manipulation of Intrathoracic Pressure," IEEE Trans. Biomedical Engineering, vol. BME-34, No. 9, Sep. 1987, pp. 738–742.

Ben-Haim, Shlomo A. et al., "A Computer Controller for Vest Cardiopulmonary Resuscitation (CPR)," IEEE Trans. Biomedical Engineering, vol. 35, No. 5, May 1988, pp. 413–416.

Newton, Joseph R. et al., "A Physiologic Comparison of External Cardiac Massages Techniques," J. Thoracic and Cardiovascular Surgery, vol. 5, No. 5, May 1988, pp. 892–901.

Swenson, Robert D. et al., "Hemodynamics in Humans During Conventional and Experimental Methods of Cardiopulmonary Resuscitation," Circulation, vol. 78, No. 3, Sep. 1988, pp. 630–639.

Deshmukh, Hanumant G. et al., "Mechanism of Blood Flow Generated by Precordial Compression During CPR," Chest, vol. 95, No. 5, May 1989, pp. 1092–1099.

Brochure, "Sequential External Counterpulsation for the Treatment of Ischemic Heart Disease," Cardiomedics, Inc., Mar. 1990.

Well, Max Harry et al., "The Clinical Rationale of Cardiopulmonary Resuscitation," Disease-a-Month, Aug. 1990, pp. 423–468.

Chandra, Nisha C. et al., "Vital Organ Perfusion During Assisted Circulation by Manipulation of Intrathoracic Pressure," Circulation, vol. 84, No. 1, Jul. 1991, pp. 279–286.

Beattle, Charles et al., "Mechanisms of Blood Flow During Pneumatic Vest Cardiopulmonary Resuscitaiton," J. Appl. Physiol., 1991.

Kuhn, Clemens et al., "Evidence for the 'Cardiac Pump Theory'," Resuscitation, vol. 22, 1991, pp. 275–282.

Cohen, Todd J., et al. "Active Compression-Decompression Resuscitation in Humans Improves Cardiopulmonary Circulation," JACC, vol. 19, No. 3, Mar. 1992, p. 27A.

"'Active Compression-Decompression Resuscitator' Investigated," Biomedical Technology Information Service, May 1992, p. 100.

"New Approaches to CPR," JAMA, vol. 267, No. 21, Jun. 3, 1992, pp. 2940–2941.

Cohen, Todd J. et al., "Active Compression-Decompression," JAMA, vol. 267, No. 21, Jun. 9, 1992, pp. 2918–2923.

Robertson, Colin et al., "Compression Techniques and Blood Flow During Cardiopulmonary Resuscitation," Resuscitation, vol. 24, 1992, pp. 123–132.

"Call a Plumber," The Practical Homeowner, Mar./Apr. 1993, p. 16.

FIG. 1A
FIG. 1B
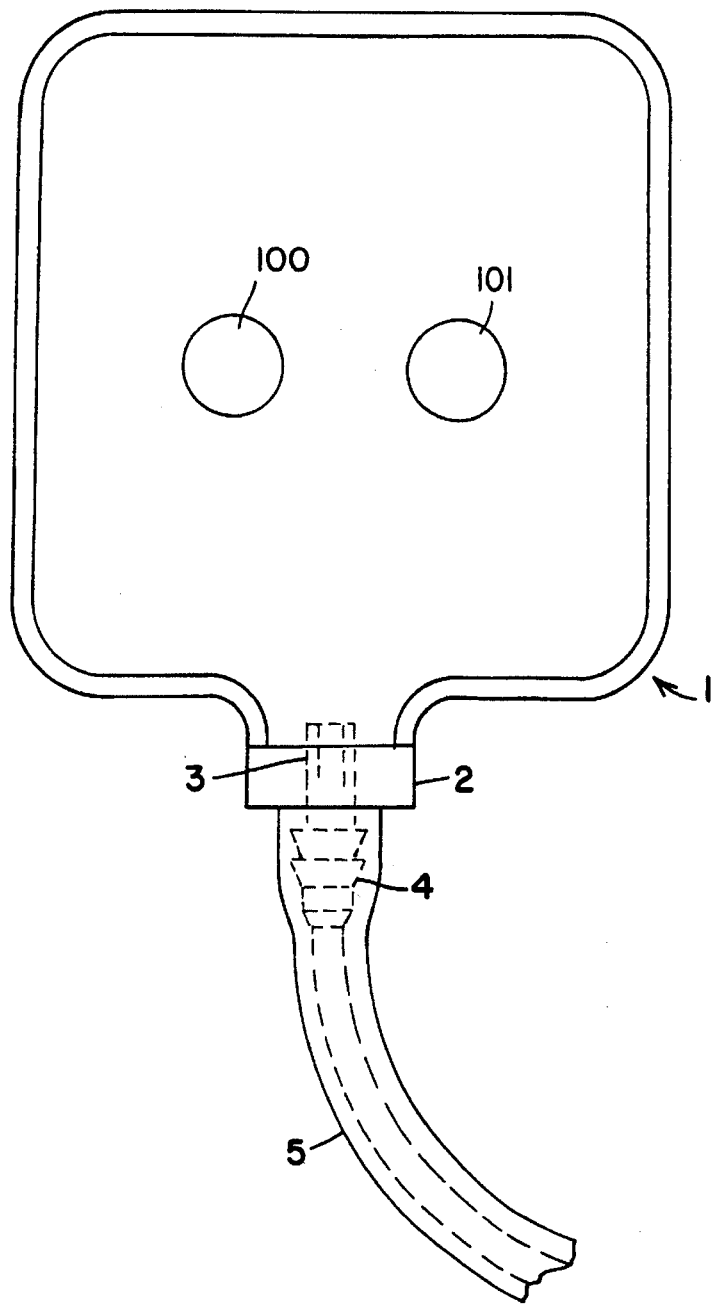
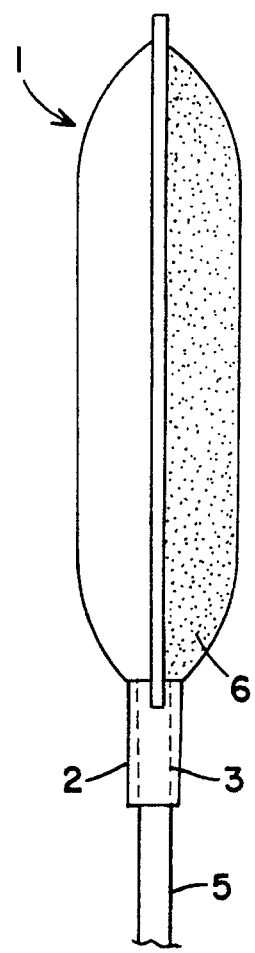

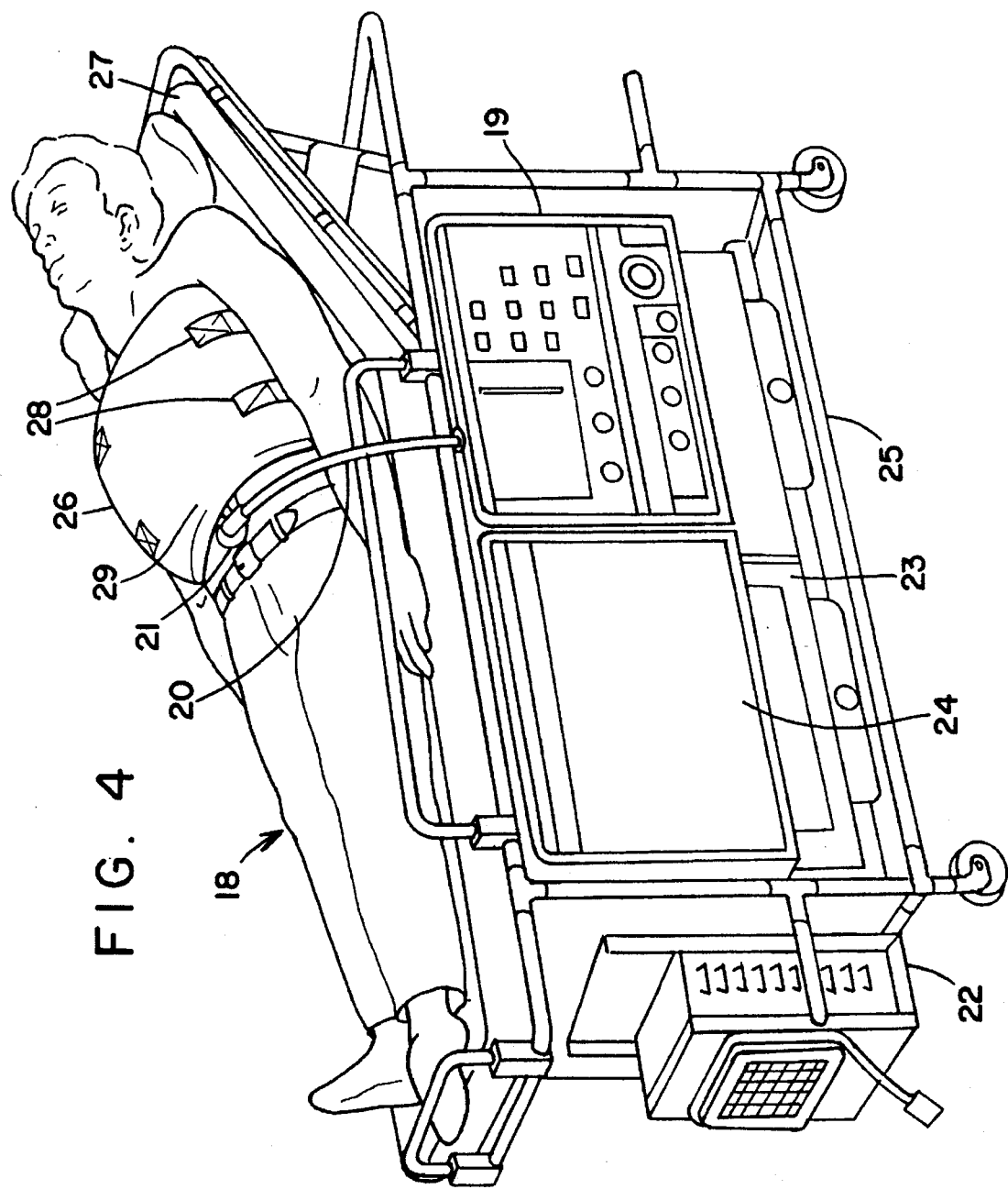

FIG. 5A ECG Waveform
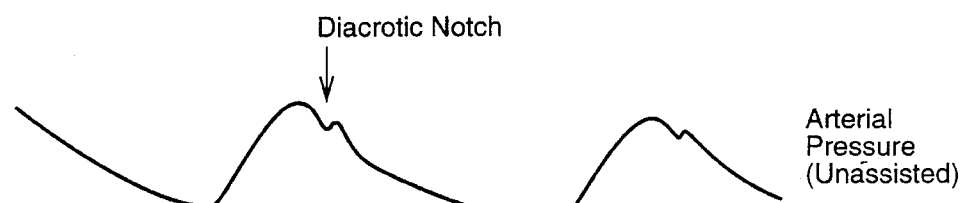
FIG. 5B Arterial Pressure (Unassisted)
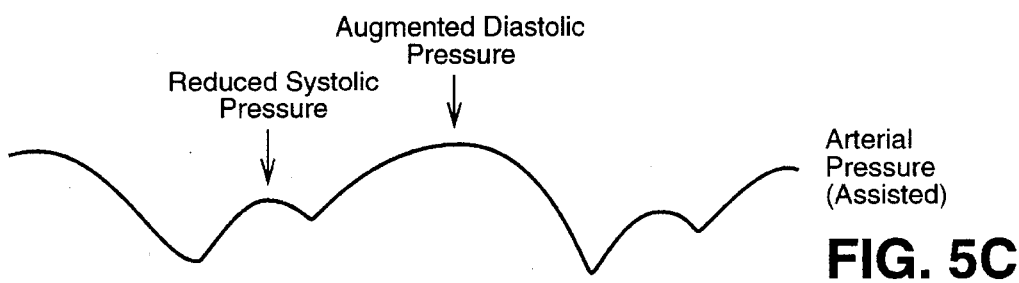
FIG. 5C Arterial Pressure (Assisted)
FIG. 5D Lateral Bladder Inflation Timing
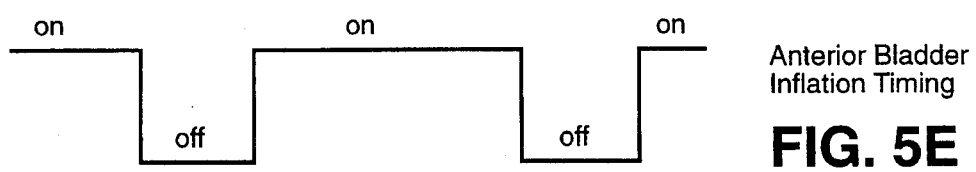
FIG. 5E Anterior Bladder Inflation Timing

ACTIVE COMPRESSION/DECOMPRESSION CARDIAC ASSIST/SUPPORT DEVICE AND METHOD

BACKGROUND OF THE INVENTION

1. Field of the Invention

This invention relates generally to cardiopulmonary support equipment, and more particularly, to non-invasive cardiopulmonary equipment which can both assist or entirely replace the natural function of a patient's heart and lungs.

2. Description of the Related Art

There are approximately 550,000 cases annually of cardiac arrest in the U.S. Despite advances in many other areas of medicine, the survival rate for these cases remains low. In general, for the victims to survive, it is essential that they receive proper resuscitation as soon as possible after the cardiac arrest. Successful cardiopulmonary support should be established within 4–5 minutes of cardiac arrest. Beyond this, any delay in providing support may result in severe brain damage.

There are two general classes of cardiopulmonary support: invasive and non-invasive. Examples of invasive support devices include percutaneous bypass, direct coronary perfusion, the Anstadt cup, hemopumps, and intraortic balloon pumping. Of course since these techniques require the insertion of devices into the body, they can only be performed by trained medical personnel. In fact, these techniques are generally not suited for emergency life support outside a hospital.

Non-invasive devices tend to be easier and less expensive to use than the invasive equipment. Non-invasive support techniques include cardiopulmonary resuscitation (CPR), leg compression, and thumper devices or compression vests which mechanically compress the chest to simulate CPR.

CPR provides cardiac support through a series of rhythmic compressions of the victim's thorax, alternating with mouth-to-mouth resuscitation. The principle advantage of CPR is its relative simplicity. An individual can be trained to administer CPR in only about 15 hours, and CPR does not require any specialized equipment.

However, CPR is not the ideal form of cardiopulmonary support; it is tiring to administer, and the thoracic compressions can severely injure a patient. Moreover, CPR is not very efficient, and ordinarily provides barely enough cardiopulmonary support to sustain the patient until professional emergency medical care can be provided.

The thumper devices and compressive vests now used for non-invasive life support have been designed to duplicate the movements used to perform CPR, the idea being to provide a mechanical substitute for a person trained to administer CPR. Examples of such devices can be found in U.S. Pa. No. 3,219,031, No. 3,509,899, No. 3,896,797, and No. 4,397,306. These patents describe devices which use reciprocable plungers to compress a victim's chest along with a means of ventilating the victim, such as a source of pressurized oxygen or a squeeze bag. However, such devices, because they are fairly complex and not easily used by untrained lay persons, are in fact less-than-ideal substitutes for a trained CPR administrator. Moreover, they suffer from the same drawbacks as manual CPR. For example, if the device is not properly positioned, the chest compressor may cause severe damage to the victim's thorax, and may not even support the cardiac function.

As an alternative to the use of mechanical chest compressors, U.S. Pat. No. 2,071,215, No. 4,424,806 and No. 4,928,674 describe how to support the pulmonary and/or cardiac functions by providing an inflatable bladder around the patient's chest. In some cases, a stiff outer shell or biasing cuff surrounds the bladder so that when the bladder is periodically inflated, the patient's chest is compressed, causing expiration and inspiration.

Because none of these devices is entirely satisfactory, CPR remains the most common resuscitative technique used by lay persons to treat cardiac arrest.

As previously noted, emergency medical personnel have available to them a number of different ways to treat cardiac arrest. However, none of these techniques are entirely satisfactory. Thus, there is a need for a CPR resuscitation device which is simple, easy to use, and not harmful to patients.

If the patient's heart is weakened, but still beating, it may be beneficial to reduce the burden on the heart. If cardiac assistance is rendered to a conscious patient, it is also important that this be done in a way which does not unnecessarily discomfort the patient.

Therefore, there is also a need for a device which can assist a beating heart even while the patient is conscious. It is also desirable that such assistance not unduly discomfort the patient.

A patient suffering cardiac arrest also requires pulmonary support, since breathing stops during cardiac failure. Accordingly, a cardiopulmonary support device must also in some way provide a substitute for breathing.

Heretofore, this has been accomplished by ventilating the patient's lungs using a source of pressurized air or oxygen. Typically, this was done by intubating the patient and then filling the lungs with fresh air or oxygen at approximately the normal breathing frequency.

A recent study determined that where cardiac support is provided by rhythmic chest compressions, cardiac output can be significantly improved by alternating chest compressions with chest decompressions. In this study, the chest was compressed and decompressed using a rubber plunger, which alternately applied pressure and suction to the patient's chest. See Cohen, T. J., et al., "Active Compression-Decompression: A New Method of Cardiopulmonary Resuscitation", J. Am. Med. Assoc. Vol. 267, No. 21, pp. 2916–23, 1992. This technique is known as active compression-decompression CPR ("ACD CPR").

In tests, when a 30 lb. anterior force was applied to the thorax of an adult male, blood pressure measured by a finger plethysmograph was increased by approximately 10 mm Hg in response thereto. Then, when a 30 lb. lateral force was applied, the blood pressure dropped by approximately 16 mm Hg.

Cadaver tests have confirmed the effectiveness of ACD CPR. Anterior compression of the cadaver thorax increased aortic blood pressure by approximately 76 mm Hg. Lateral compression of the thorax decreased blood pressure by approximately 12 mm Hg, as did anterior suction of the thorax.

ACD CPR is significantly more effective than conventional "compression-only" CPR. It provides both perfusion and ventilation, and can resuscitate patients where conventional CPR and defibrillation fail. However, the plunger used to decompress the chest introduces a number of complications. For example, since decompression requires a vacuum be maintained between the plunger and the chest, it is imperative to provide a good seal between the plunger and the chest. Moreover, since people of all ages suffer cardiac arrest, it is necessary to be able to treat people of all sizes. Accordingly, a range of different size and shape plungers may be needed. Even then, if the patient is hirsute, heavily-muscled, or large-breasted, it may prove impossible to provide a seal which allows adequate decompression.

Thus, there exists a need for a support device which compresses and decompresses the patient's chest without using a plunger, and which device is sufficiently flexible to accommodate a wide range of victim body types.

SUMMARY OF THE INVENTION

The present invention involves a device for compressing and decompressing a patient's thorax, which includes compressing means for applying anterior pressure to compress and increase the pressure in the thorax and decompressing means for applying lateral pressure to circularize and decrease the pressure in the thorax.

Another embodiment of this invention concerns a device for compressing and decompressing a patient's thorax that includes a first thoracic compressor suitably dimensioned and disposed to cover at least a portion of an anterior region of the thorax, this first thoracic compressor being positioned adjacent to the thorax, and a second thoracic compressor suitably dimensioned and disposed to cover at least a portion of a lateral region of that thorax, the second thoracic compressor being positioned adjacent to the thorax. Means are provided to urge the thoracic compressors against the thorax, such that when a particular thoracic compressor is actuated, the urging means causes that thoracic compressor to press against the thorax, and a compression controller can sequentially actuate and deactuate the first and second thoracic compressors. Thus, when the first thoracic compressor is actuated, the thorax is compressed, and pressure in the chest is increased, and when the second thoracic compressor is actuated, the thorax is consequently decompressed and pressure in the thorax is decreased.

Yet another embodiment of this invention relates to a device for compressing and decompressing a patient's thorax, including a first thoracic compressor and a first opposing surface, each being dimensioned and disposed so that when a patient is placed therebetween, the first thoracic compressor and first opposing surface are respectively positioned anteriorly and posteriorly adjacent to the thorax. Similarly, a second thoracic compressor and a second opposing surface are provided, each being dimensioned and disposed so that when the patient is placed therebetween, the first thoracic compressor and second opposing surface are positioned adjacent to and alongside of the thorax. Additionally, a compression controller sequentially actuates and deactuates each of the first and second thoracic compressors, so that when the first thoracic compressor is actuated, the thorax is consequently compressed and pressure in the thorax increases, and when the second thoracic compressor is actuated, the thorax is consequently decompressed and pressure in the thorax is decreased.

A further refinement of this invention is a device for compressing and decompressing a patient's thorax, comprising a first inflatable bladder and a first opposing surface, each dimensioned and disposed so that when a patient is placed therebetween, the first bladder and first opposing surface are respectively positioned across an anterior part and a posterior part of the patient's thorax. A second inflatable bladder and second opposing surface are included, each dimensioned and disposed so that when the patient is placed therebetween, the second bladder and second opposing surface are positioned across at least a part of lateral regions of the thorax, and an inflation controller sequentially inflates and deflates the bladders so that when the first bladder is inflated, the thorax is compressed and pressure in the thorax is increased, and when the second bladder is inflated, the thorax is decompressed and pressure in the thorax is decreased.

In another preferred embodiment of this invention, the device for compressing and decompressing the patient's thorax includes first, second and third thoracic compressors, the second and third compressors acting in opposition, and the three compressors being dimensioned and disposed about the patient so that the first thoracic compressor is positioned across at least a part of an anterior region of the thorax, and the second and said third thoracic compressors are each positioned across at least a part of lateral regions of the thorax. A compression controller sequentially actuates and deactuates the first, second, and third compressors so that when the first compressor is actuated, the thorax is compressed and pressure in the thorax is increased, and when the second and third compressors are actuated, the thorax is decompressed and pressure in the thorax is decreased.

A similar embodiment of this invention uses inflatable bladders for the first, second, and third thoracic compressors, and also includes urging means for urging the bladders against the thorax so that when a particular bladder is inflated, the urging means causes that bladder to press against the thorax. This embodiment also includes an inflation controller for sequentially inflating and deflating the bladders. This allows pressure in the thorax to be increased and decreased.

Still another embodiment employs two pairs of opposed bladders, one pair to compress and the other to decompress the thorax. In the first pair, one bladder is positioned anteriorly and the other posteriorly, both adjacent the thorax. In the second pair, one bladder is placed on left side of the patient and the second one on the right side, again, both being adjacent the thorax. When the compression controller inflates the first pair, the thorax is compressed and pressure in the thorax increases. When the first pair is deflated and the second pair inflated, the thorax is decompressed and pressure in the thorax is decreased.

This invention also relates to a method for compressing and then decompressing a patient's thorax, including the steps of applying at least one of anterior pressure and posterior pressure to the thorax, thereby compressing and increasing the pressure in the thorax, and relieving the at least one of anterior pressure and posterior pressure, applying lateral pressure to the thorax, thereby decompressing and decreasing pressure in the thorax, and relieving that lateral pressure.

BRIEF DESCRIPTION OF THE DRAWINGS

FIG. 1A is a plan view of a compression bladder which can be used in the practice of the instant invention.

FIG. 1B is a side view of the bladder shown in FIG. 1A.

FIG. 4 is a perspective view showing the patient of FIG. 3 with a vest placed around his chest and over the three bladder set.

FIGS. 5A–5C depict, respectively, a patient's ECG waveform, unassisted arterial pressure over time, and arterial pressure when the patient is assisted by the present invention.

FIGS. 5D and 5E are logic diagrams for bladder inflation of the ACD vest of the present invention being used in the assist mode.

DESCRIPTION OF THE PREFERRED EMBODIMENTS

Figure 2:
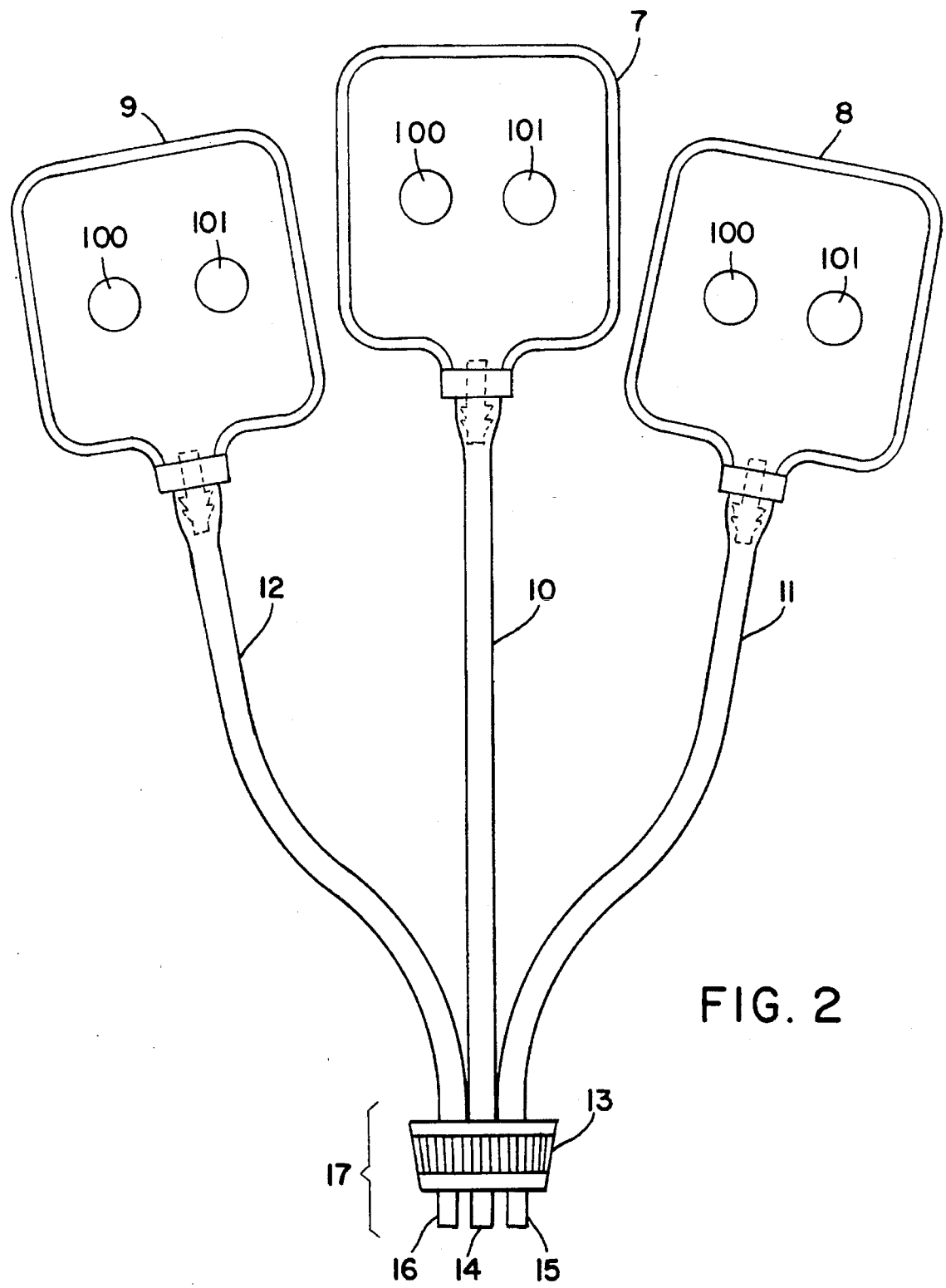
FIG. 2 is a plan view of a bladder set comprised of three bladders.

A first embodiment of the present invention provides both cardiac and pulmonary support by alternately compressing and decompressing the patient's thorax. Cardiac assistance can be provided by suitably regulating the amount of compression and decompression.

The present invention is intended to avoid the shortcomings of prior art equipment. When one compresses and decompresses the thorax by applying force using the plunger taught by the prior art, the force is distributed over only a small region of the thorax. This is undesirable, since even moderate forces applied over small areas can produce pressures high enough to cause bodily harm, or at least significant patient discomfort.

The present invention is based in part on the discovery that chest compression occurs when the thorax is forced to take on a particular shape, and chest decompression occurs when it is forced to take on a different shape. The present invention performs ACD CPR by changing the shape of the patent's chest between that associated with compression and that associated with decompression.

Another benefit of this invention is that pulmonary support is provided by the same movements which substitute for cardiac function. That is, whenever the thorax is compressed to pump blood away from the heart, the lungs are compressed, and stale gas is expelled therefrom. Then, as the thorax is decompressed to draw blood toward the heart, the volume of the lungs increases, and fresh air is drawn in.

Although each chest compression/decompression cycle may not exchange a volume of air comparable to that of a normal breath, because these compressions and decompressions occur at a rate about the same as the patient's normal resting heartbeat, a rate which is still greater than the normal at rest respiratory rate, the volume of air flowing through the lungs will approach that of a healthy, unassisted patient. In other words, when the present invention is employed, the patient is caused to take shallow breaths but at a frequency higher than that for normal respiration.

Although this invention is believed to be able to provide a level of pulmonary support sufficient for life support, it may be advantageous to render additional pulmonary assistance. This can be done using conventional medical techniques. For example, small perforated tubes can be placed near or in the patient's nostrils and oxygen-enriched gas can be introduced to increase the amount of oxygen in the breathing air. Alternatively, the patient's face can be covered by an oxygen mask.

If it is desired to further increase the volume of gas exchanged during ACD CPR, the patient can be fitted with a pressurized gas mask. Alternatively, a "jet" or conventional ventilator could be used.

The present invention preferably uses several inflatable bladders selectively to vary the shape of the patient's chest.

However, this invention is not confined to the use of inflatable bladders; rather, any equipment capable of producing the appropriate thoracic displacements can be used. Such equipment includes hydraulic or pneumatic pistons, solenoids and mechanical linkages, such as a scissors linkage. Of course it will be apparent that such equipment must be operated in a manner which avoids applying excessively high forces and pressures to the chest, since the excessive force or pressure could break ribs or otherwise injure the patient.

Chest compression occurs when the anterior and posterior thorax surfaces are moved toward one another, "flattening" the chest (anterior refers to the front of the thorax, posterior, the back). Chest compression is accompanied by an increase in the pressure within the thoracic cavity, and a decrease in the volume of the lungs. The increased intra-thoracic pressure forces blood out toward the brain and extremities, while the decrease in lung volume drives carbon dioxide laden gas out from the lungs.

Chest decompression occurs when the two lateral surfaces of the thorax are moved toward each other, "circularizing" the chest. As the chest is decompressed, the pressure within the chest falls and the volume of the lungs increases. Due to the reduced intra-thoracic pressure, blood is drawn toward the heart. At the same time, fresh air flows into the lungs.

The present invention circularizes the thorax in a novel way, one which is significantly more comfortable than any decompression method used heretofore.

In the preferred embodiment, the apparatus has an anterior bladder and two lateral bladders disposed around the patient. Each bladder is connected to a source of pressurized fluid, and possibly a vacuum, by a controller, which regulates inflation and deflation of the respective bladders.

By sequentially periodically inflating and deflating these bladders, the patient's chest can be rhythmically compressed and decompressed. The bladders can be either elastic or inelastic; the membrane of an elastic bladder stretches as the pressure inside the bladder increases, whereas the membrane of an inelastic bladder does not.

It is also desirable to provide structure, preferably in the form of a harness or vest, which confines the bladders so that any expansion is directed inward, causing the bladders to press against the patient's thorax. Without such an expansion limiting structure, the inflated bladders would have a tendency simply to expand away from the patient's thorax, and no pressure would be exerted thereon.

This constraining structure can take the form of a rigidifying vest which surrounds the bladders. Such a vest may include a relatively flat, stiff backboard disposed beneath the patient. The board can be either a separate structure or an integral part of the vest. This board serves a dual function, allowing the patient to be transported while ACD CPR is being performed, and serving to oppose the pressure applied to the patient's thorax by the anterior balloon. If desired, this board can be covered with some sort of conformable flexible material which adapts to the shape of the patient's back. Such flexible material will help distribute force across the back and may improve patient comfort. Of course, care must be taken that the flexible material not absorb so much of the pressure being exerted that thoracic compression or decompression is compromised.

Although the backboard could be omitted, it is thought to be preferable to use the board. Besides facilitating conveyance, the board helps to distribute the pressure applied to the thorax during compression. The board also helps keep the patient's body flat during compression; without it, the pressure applied by the inflating anterior balloon will tend to curve the patient's body so that the sides of the thorax move toward one another. This movement is undesirable, since it reduces pumping efficiency. Although ACD CPR may be performed in this manner, it is believed to be preferable to avoid flexing the patient's body this way, since it may unduly stress and consequently injure the victim.

FIGS. 1A and 1B depict a bladder 1 useful in practicing the present invention. Bladder 1 is preferably made of plastic, but other materials, for example, rubber are also suitable candidates. It can be fabricated, for example, by heat sealing around the edges of two plastic sheets or it can be made by using traditional rotational or blow molding techniques. Heat sealing may be most economical, while the molding techniques may produce a more durable product.

Bladder 1 is provided with a collar 2 and a port 3. Port 3 is provided with a barbed fitting 4. Connecting tube 5 is designed to fit over barbed fitting 4 and the barbs on fitting 4 are designed to assure a mechanically as well as pneumatically secure connection. Other methods for joining tube 5 to port 3 could also be used, for example, gluing, ultrasonic welding or RF welding.

To maintain stable positioning of bladder 1, a portion or all of one face can be provided with an adhesive surface 6. When not in use, the adhesive surface can be protected with a release liner (not shown). In addition, the adhesive surface contacting the patient's skin can incorporate an ECG or defibrillator electrode 100, 101 or a combination of those. The electrode leads (not shown) can be integral with or separate from the tubing 5.

The bladder is designed to deliver the forces and displacements required for the CPR application. Preferably, that force will be about 60 lb. and the displacement will be about 2 inches. When the bladder-skin contact area is about 16 square inches and the inflated bladder is about 2 inches thick, 60 lb of force requires the delivery of about 32 cubic inches of air at 3.75 psi. Obviously, a larger bladder will need a greater volume of air but at lower pressure. Conversely, a smaller bladder will require less air but at higher pressure. Selection of the ideal bladder size for a particular application will depend upon a number of factors, including the anatomy of the patient, the pressure which it is desired to exert and the available pneumatic pump.

While the above discussion has identified air as the preferred working fluid, those skilled in the art will recognize that almost any other gas and even some liquids could be used instead.

Several bladders like that shown in FIG. 1 can be combined in a bladder set. One such set, comprised of three bladders, is shown in FIG. 2. That three bladder set is comprised of one anterior bladder 7 and two lateral bladders, a left lateral bladder 8 and a right lateral bladder 9. The connecting tubes 10, 11 and 12 from those bladders lead into manifold 13. Manifold 13 is provided with three individual connectors, 14, 15 and 16 which are attached in fluid tight fashion to tubes 10, 11 and 12 respectively. Connectors 14, 15 and 16 and manifold 13 combine to form a unified connector 17. This unified connector can be fabricated as a single piece, for example by injection molding.

The ACD pump is preferably provided with a mating connector (not shown) to facilitate rapid connection of the pump to the bladders. In addition, it is preferable to employ a locking mechanism (not shown) to prevent the mating connectors from separating. When the mating connectors are together, there should be a continuous fluid-tight path from the ACD pump to each bladder.

Figure 3:
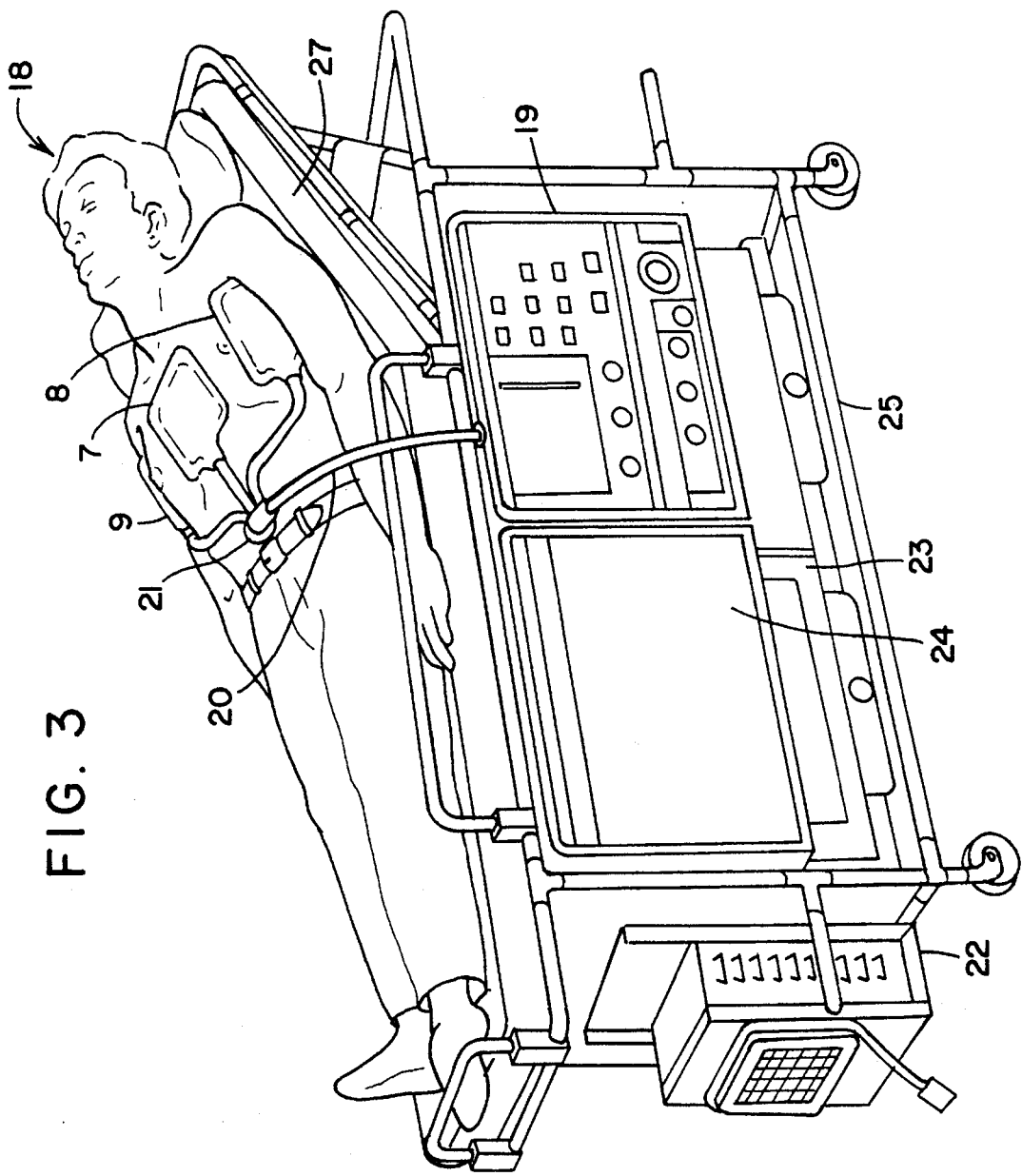
FIG. 3 is a perspective view showing a patient with the three bladder set of FIG. 2 placed adjacent his thorax.

Referring now to FIG. 3, the orientation of anterior bladder 7 and lateral bladders 8 and 9 can be seen relative to the patient 18. These are connected to ACD pump/controller 19 by pneumatic line 20. Line 20 has at least two lumens to provide independent inflation and deflation of the anterior bladder on one hand and the lateral bladders on the other. One lumen is connected to anterior bladder 7 and the other to lateral bladders 8 and 9. The line 20 connects securely to the bladder set connector 17 with connection means 21, which is ideally air-tight and self-locking.

This Figure shows one possible arrangement of ACD Pump/Controller 19, power supply 22, batteries 23, storage compartment 24, and gurney 25. This arrangement would be ideal for in-hospital or ambulance operation. Alternative arrangements would also be possible, such as a self-propelled transport unit (e.g., a "stretch golf cart" with integral ACD device), or a simple portable unit without a gurney, having a compact backboard to which the vest can be secured.

Referring now to FIG. 4, an ACD vest 26 is shown positioned over the bladders. The vest and underlying patient support 27 provide stable, near-rigid surfaces which permit the bladders effectively to exert forces on the patient. One possible vest design would be based on the use of a constrained volume of particulate (such as polystyrene beads 126). The vest could, for example, be made of PVC and have several evacuable chambers, each filled with polystyrene beads. Application of vacuum to the vest interior rigidifies the structure by preventing relative motion of the particulate. The vacuum could be provided by a vacuum pump integral to the ACD unit. Of course it will be appreciated that the relative rigidity of the vest can be controlled by suitably regulating the vacuum drawn on the evacuable chambers. For optimal effectiveness and flexibility, the vest could be adjusted for fit to the patient with hook and loop or strap fasteners 28.

In another embodiment, an additional bladder could be provided for abdominal compression or constraint at point 29. This would possibly enhance the hemodynamic benefits of the device, or give a Heimlich maneuver when airway obstruction occurs. The abdominal bladder could be inflated and deflated simultaneously with the anterior bladder, or it could be inflated and deflated independently, for example, to produce the Heimlich maneuver effect.

Alternatively, the abdominal bladder could be kept continuously inflated to a predetermined volume or pressure while ACD CPR is being performed. Keeping the abdominal bladder inflated while anterior compression is underway may increase the effectiveness of the procedure by preventing the organs in the thorax from being squeezed into the abdominal cavity. This might also be accomplished by configuring the vest so that when it is rigidified, it automatically exerts pressure on the abdomen.

Figure 6:
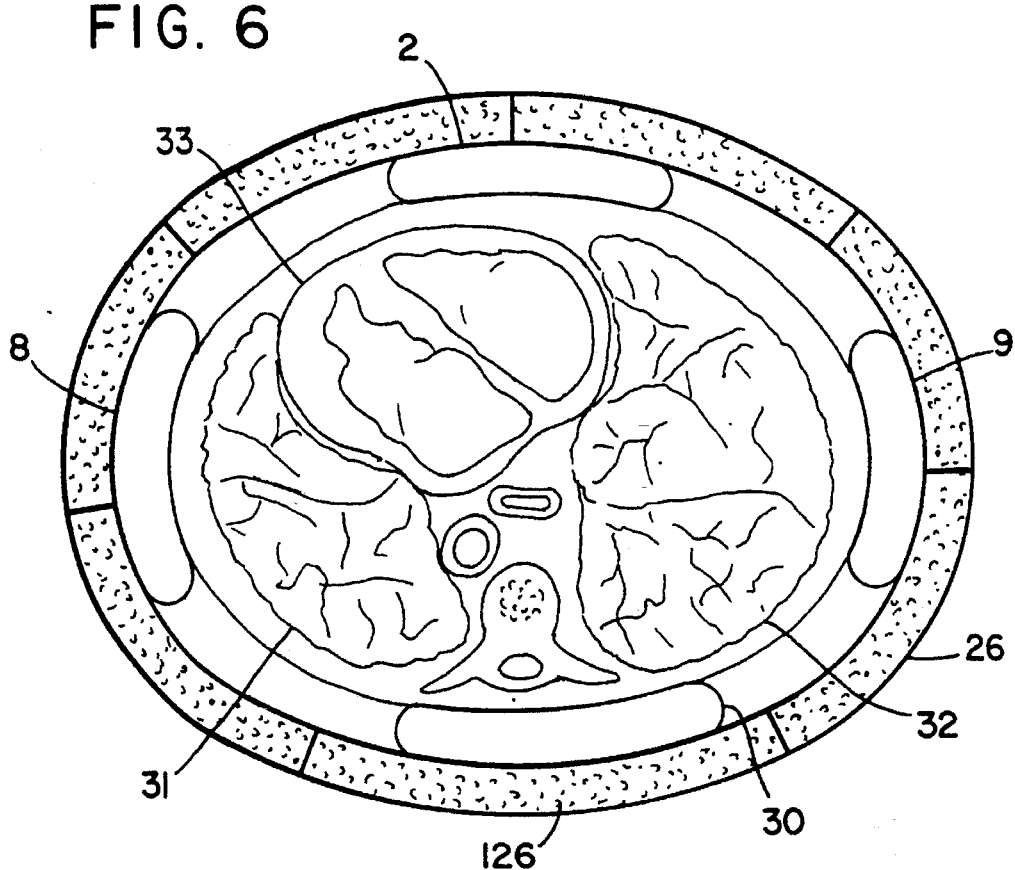
FIG. 6 is a schematic cross-section view taken through the thorax of a patient with a four bladder vest applied.

Referring next to FIG. 6, there is shown a cross section of a patient's thorax with a four bladder vest applied. As can be seen, in this embodiment vest 26 surrounds the entire thorax. Anterior bladder 2, posterior bladder 30 and lateral bladders 8 and 9 are all confined between vest 26 and the patient's thorax. Inflation of bladders 2 and 30 causes the thorax to flatten out into more of an ellipse. This tends to squeeze the lungs 31 and 32 so that carbon dioxide-laden air is expelled. At the same time, the heart 33 is also compressed so that blood is forced out into the pulmonary arteries and the aorta. When the anterior and posterior bladders 2 and 30 are deflated and lateral bladders 8 and 9 are inflated, just the opposite occurs. The thorax is forced into a more rounded and less elliptical shape, thereby causing both the lungs and heart to expand to draw fresh air into the lungs and blood into the heart.

Figure 7:
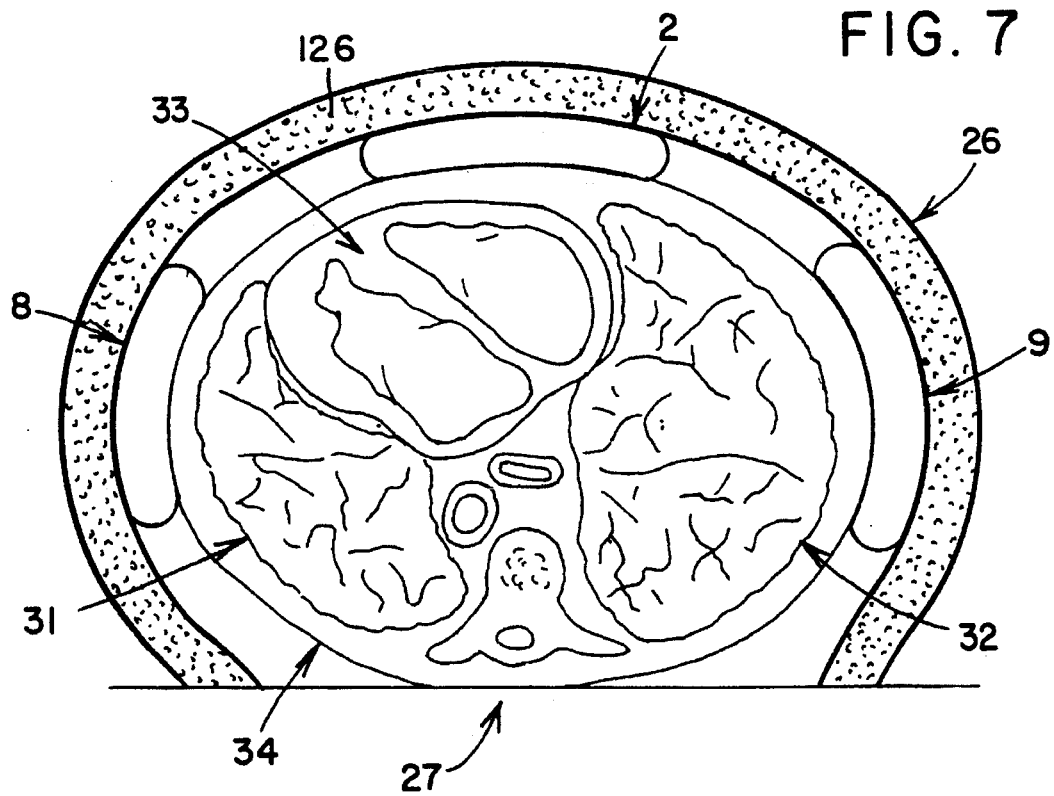
FIG. 7 is a schematic cross-section view taken through the thorax of a patient with a three bladder vest applied.

FIG. 7 is similar to FIG. 6 except that in FIG. 7 the vest 26 only has three bladders, an anterior bladder 2 and two lateral bladders 8 and 9. Instead of a posterior bladder, in this embodiment the posterior of the thorax 34 rests against a rigid or semi-rigid support 27. It will be understood that this invention also encompasses the use of a single posterior bladder and a stiff anterior surface.

Not shown are optional integral ventilator and/or defibrillator. These could be essentially similar to existing stand-alone devices. For optimal performance, a central controller would coordinate the actions of ACD, defibrillator, and ventilator. Ventilation control, for example, might enhance the hemodynamic effects of ACD, if properly timed. Likewise, automatic defibrillation could be linked to detection of appropriate ECG conditions.

It should be understood that in all of the embodiments described herein any one or more of the individual bladders could be replaced by two or more smaller bladders. It will also be appreciated that some sort of stiffening sheet could be provided between each bladder and the thorax. That sheet could be made of a rigid material or alternatively, it could be made of a flexible or conformable material.

One benefit of the vest of the present invention is that it allows ACD CPR to be performed in emergency situations, where there is little time to prepare the equipment. This vest is preferably of a size and style which allows ACD CPR to be performed on a range of differently sized patients. Alternatively, it may be preferable to provide a set of vests, each fitting a range of patient sizes, so that ACD CPR can be performed on all victims, whether infant or large adult male. Vest size can easily be adjusted by use of Velcro® fasteners or buckles, and since the design of such adjustable vests is well-known, vest construction will not be discussed further.

It will also be appreciated that the compression bladders can either be integrated into the structure of the rigidifying vest itself, or can be placed on the patient first and then the vest wrapped therearound.

Since the bladders and rigidifying vest cover the patient's thorax, it may be difficult to obtain access thereto. For this reason, it may be helpful to provide the various bladders with electrodes and electrical sensor pads which allow the taking of an electrocardiogram or other ECG monitoring, measurement of other bodily electrical signals, and even pads which can be used for emergency defibrillation. These electrodes and pads can be attached to the bladders or can simply be attached to the patient before the bladders and vest are put on.

It will also be appreciated that other rigidifying harness designs may be just as useful. For example, a vest consisting of an adjustable mechanical framework might be employed. Such a device could consist of a set of metal slats joined in such a way that they are easily positioned around the thorax, and are able to resist bladder expansion.

Bladder inflation and deflation are regulated by a controller. This controller may consist of a regulating section, and an actuation section consisting of a set of valves which controllably connect the bladders to the pressurized fluid supply and possibly a vacuum line.

To inflate a bladder, the controller opens the valve which allows fluid to flow from the pressurized fluid supply to the bladder. After a time sufficient for the bladder to fill, the valve closes. Then, to empty the bladder, another valve opens and allows fluid to flow from the bladders to either the atmosphere, a vent line, or a source of vacuum.

If desired, the working fluid circuit can be closed so that fluid leaving the bladders is repressurized and reused in later bladder inflations. Alternatively, open fluid circuits using water, air, or any other suitable working fluid can be employed.

Preferably, the valves used to regulate fluid flow can be opened and closed by suitable electrical signals. This facilitates bladder actuation/deactuation, since electronic control systems suitable for operating electrically-actuated valves are widely known.

Preferably, the controller which regulates valve actuation is programmable and can respond to changes in the patient's condition. It is envisioned that an ideal controller would be preprogrammed so that users would only have to enter patient size—the controller would then select the proper bladder inflation/deflation rate. Of course it is possible to provide a sequencer which allows the user to regulate aspects of the bladder inflation/deflation such as rate of inflation/deflation, bladder volume change, and idle time. This sequencer can also be used to control evacuation of the rigidifying vest.

To compress the patient's chest, the rigidifying vest is securely fastened about the thorax and is then evacuated. This renders the vest relatively rigid and unyielding. Next, the anterior bladder is inflated. Because of the rigidifying vest, the bladder can only expand inward toward the patient's thorax. As the fluid pressure increases, the bladder increases in volume and begins pressing against the thorax. As the anterior surface of the thorax moves, the thorax is compressed, and the pressure in the thorax rises. It is believed to be this elevated thoracic pressure that causes blood to circulate out to the brain and other extremities.

Once the thorax has been fully-compressed, it is necessary to decompress the thorax so that the heart can refill with blood and the thorax can expand, allowing fresh air to flow into the lungs. To do this, it is not enough merely to release the pressure in the anterior bladder. When that happens, the thorax decompresses, but not by an amount sufficient to draw a meaningful quantity of deoxygenated blood into the victim's heart, and fresh air into the victim's lungs.

Instead, the lateral bladders are sized and positioned so that they can apply force in a way which provides adequate chest decompression. Specifically, the two bladders are located on the sides of the thorax, and when inflated, they force those sides toward one another. This has the effect of circularizing the thorax and raising the anterior thoracic surface, which decompresses the thorax. Now, deoxygenated blood flows into the chest (the valves of the heart and vascular system ensure one-way blood flow) and air flows into the lungs. After the thorax is sufficiently decompressed, the lateral bladders are deflated, and another thoracic compression can begin.

It is contemplated that bladder inflation does not begin until after the emptying bladder(s) is evacuated, so that the patient experiences separate, defined compressions and decompressions. However, it is also within the scope of this invention to sequence inflation and deflation of the different bladders with some overlap.

In addition, it may be helpful to vary the rigidity of the rigidifying vest through a compression/decompression cycle by changing the vacuum applied thereto. By reducing the vest's rigidity slightly during decompression, the volume of air flowing into the lungs may be increased.

This compression/decompression system can be used either for total life support, as where a patient has suffered cardiac arrest, or for assistance, as where a patient's heart is in a weakened, but still functional state. Such weakened cardiac performance may occur, for example, when a patient has suffered cardiogenic shock, acute myocardial infarction, refractory ventricular failure, or septic shock. The different modes of operation will differ principally by the magnitude of the pressures exerted on the patient's chest. They may also differ in the rate of compression/decompression.

Where the patient is in cardiac arrest, compression and decompression can occur at any rate; however, if the patient's heart is still beating, it will be helpful to synchronize chest compression (anterior bladder inflation) with cardiac diastole, to raise aortic pressure and cardiac output, and similarly to synchronize chest decompression (lateral bladder inflation) with systole, to reduce aortic pressure and thereby lessen the work required for ventricular ejection.

Referring now to FIGS. 5A–5B, a probable logic sequence for operation of the ACD device in "assist mode" is shown. This logic essentially mimics that employed for intra-aortic balloon pumping. As depicted in FIG. 5, ideally, the anterior bladder should be inflated immediately following the diacrotic notch in the arterial pressure wave and remain inflated until the onset of systole, at which time the lateral bladders are inflated.

As can be seen in FIGS. 5A–5B, when this sequence is followed, the normal arterial pressure wave is modified so that systolic pressure just prior to the diacrotic notch is reduced and diastolic pressure between the dicrotic notch and the onset of systole is increased.

In an ACD device according to the present invention inflation and deflation of the bladders requires that significant amounts of working fluid be moved into and out of the bladders. Since such movement of fluid cannot be accomplished instantaneously, a timing algorithm can be employed to anticipate the diacrotic notch and the onset of systole. In this manner, the inflation/deflation cycle triggers can be made to occur slightly in advance of the diacrotic notch and systole, thereby providing for maximum inflation to occur precisely when needed. This timing algorithm can work off the R wave of the ECG or off the diacrotic notch of the arterial pressure wave.

As already noted, this invention can be used in two different modes, cardio-pulmonary support ("support") and cardio-pulmonary assistance ("assistance"). In support mode, this invention provides a complete substitute for the patient's own inactive lungs and heart. It is therefore imperative that the device pump a volume of blood and induce respiration at rates sufficient to sustain the patient.

Since the patient's own cardiac and pulmonary functions have failed, it is necessary that when used in support mode, this invention be self-pacing. This can be done by providing circuitry which causes given amounts of compression and decompression at a fixed rate. Preferably, the amounts and rates of compression and decompression are separately adjustable. These features are needed to insure that the resuscitator can be used to support patients regardless of their age, size and condition.

For example, a large patient will require more blood be pumped and more gas exchanged than a smaller patient. Likewise, a child may need to have smaller volumes of blood and air pumped at a higher rate than an adult.

In addition, depending on changes in the patient's condition, it may be necessary to vary resuscitator performance.

Since this invention is capable of both support and assistance, it would be helpful for the device to be able to determine when it is necessary to change its mode of operation.

In this regard, it would be helpful to provide means for monitoring the patient's condition, and means for using the monitored results to control the resuscitator. If the device monitors a normal QRS ECG waveform, it would operate in assist mode, since the patient's heart is still functioning. If, however, the QRS ECG waveform is lost, or cannot be detected, the device would shift into support mode, since the absence of the waveform indicates cardiac arrest.

Among the physiological signs which might be monitored and used to control operation are coronary blood flow, cardiac output, oxygen saturation, coronary perfusion pressure, peak systolic pressure, mean systolic pressure, mean arterial pressure, expired $CO_2$, blood pressure, blood flow rate in a given blood vessel, blood oxygen level, blood carbon dioxide level, and/or respiration volume.

Such control techniques are not in and of themselves a part of this invention, and are well-known. Since they are known and could be applied by one of ordinary skill in the art to the present invention, further discussion of such control systems is not believed to be necessary.

As previously explained, it may be desirable to provide the anterior and/or lateral thoracic bladders with electrode pads suitable for performing cardiac defibrillation. The apparatus could be designed to indicate to an operator the need to perform defibrillation based upon the detection of certain physiological signals, such as an ECG indicating there has been a conversion from fine V.F. (ventricular fibrillation) to coarse V.F. (this change in cardiac signal is known to occur when an arrested heart experiences an increase in coronary perfusion, as might occur after a period of ACD vest support). Further, once heartbeat has been restored, it may be desirable for the resuscitator to shift to assist mode to reduce the burden on the heart.

These different modes of operation (support and assist) may be started either manually or automatically.

Another structure which might be included in the vest is a device which performs a "Heimlich" maneuver. This device would be useful because resuscitation efforts typically begin with a "Heimlich" maneuver to ensure that the victim's respiratory tract is clear of any obstructions. This could be done by aggressively inflating an abdominal bladder, thus sharply compressing the abdomen, possibly together with inflation of one or more thoracic bladders.

In a further embodiment of this invention, operating efficiency could be improved by selectively constraining the patient's abdomen in synchronism with the compression/decompression cycle. For example, this could be accomplished by lengthening the rigidifying vest so that it reduces blood flow to the abdominal region, thereby increasing the blood flow to the brain and coronary vessels.

Still a further embodiment of this invention might also use selective abdominal compressions to augment blood flow. This could be done by providing one or more abdominal bladders, which would be actuated in some synchronism with the thoracic compressions. To enhance blood flow to the upper body, it would probably be most helpful to cause the abdominal compressions to coincide with the thoracic decompressions (lateral balloon actuation).

Improvements in performance also might be obtained by providing bladders around the patient's extremities, which bladders periodically compress and decompress those extremities.

Other embodiments of this invention may use fewer than three bladders. For example, an alternate embodiment of this invention would use only a single posterior bladder and only a single lateral bladder, which are surrounded by the rigidifying vest. Alternatively, the anterior bladder might be replaced by a posterior bladder. To improve bladder performance, and to better distribute the pressures applied to the patient, it may be helpful to place a flat, stiff surface between each side of the thorax and the adjoining bladder. Of course, this invention can be adapted to other structures and arrangements so long as these properly compress and decompress the thorax by the above-described thoracic manipulations.

It is also possible to eliminate the rigidifying vest by placing, the patient in a U-shaped enclosure (not shown), with the two lateral bladders being placed between the sides of the thorax and the enclosure walls. The patient is positioned facing upward on a relative stiff flat surface, and an anterior bladder is then placed atop the patient. It will be appreciated that while the lateral bladders are restrained by the enclosure walls so that they can only expand inward, it will be necessary to provide a cover of some sort to direct expansion of the anterior bladder inward.

Such a cover can be a flexible fabric, or one or more stiff plates. It is even possible to construct the cover in a manner similar to the rigidifying vest. Such a cover has one or more evacuable chambers, each filled with relatively incompressible beads. The edges of the cover are attached to the container walls or are otherwise restrained. Now, when the evacuable chambers empty, the cover will stiffen, and will be able to oppose the pressure which attends anterior bladder inflation.

Another method of eliminating a rigidifying vest is to use a harness comprised of bladders connected with straps and/or netting. Such a harness would be placed around the patient and the straps pulled as tight as possible. The tight straps would then ensure that most of the expansion of the expanding bladders is directed inwardly toward the thorax.

Alternatively, two harnesses could be employed, a lateral harness for the lateral bladders and an anterior/posterior harness for the anterior and/or posterior bladders. Each harness could be provided with its own tightenable straps. To further insure that adequate force is directed inwardly, the straps of each harness could be made to pass around the outside of its bladders.

A further embodiment of this invention improves performance by causing the deflating bladders to pull on the chest walls. This can be done by securing the bladders to the rigidifying vest or container wall, as well as the thorax itself. In particular, it is envisioned that the bladder could be temporarily affixed to the patient using a suitable adhesive. The bladder could be attached to the vest or wall in any well-known way.

In this embodiment, the bladders are deflated by applying a vacuum thereto. As the bladders contract, they apply tensile stress to the chest walls.

This embodiment would operate by simultaneously inflating one type of bladder (i.e. anterior) and deflating the opposing bladder (i.e. the lateral pair).

This invention can be powered in any way that permits proper operation. Depending on the environment where this invention is to be used, it may be possible to use electrical power, as would be the case when the device is used in a hospital emergency room. If the device is portable and will be used where there are no electrical power lines, it might be possible to provide a small electrical generator and simply use the standard electrically-powered device, or to provide a battery-powered version (as in FIG. 4) or a manually-operated version. In addition, stored pneumatic energy could be used, or a small gasoline engine might be employed.

Finally, it will be appreciated that this invention can be implemented by providing separate pieces of equipment, some of which is new, and some of which is well known, for example, by using a rigidifying vest, inflatable bladders, control system, conventional ECG monitor and a conventional defibrillator. Alternatively, these devices could be provided in a single integrated system. This latter approach would lend itself to portable emergency use.

It will be appreciated that the present invention is not intended to be limited to the drawings and embodiments discussed above. Numerous departures in construction, materials and operation can be made therefrom while still remaining within the scope of the claimed invention.

What we claim is:

1. A device for compressing and decompressing a patient's thorax, the patient having a heart, comprising:

a first thoracic compressor suitably dimensioned and disposed to cover at least a portion of an anterior region of the thorax, said first thoracic compressor being positioned adjacent to the thorax;

a second thoracic compressor suitably dimensioned and disposed to cover at least a portion of a lateral region of the thorax, said second thoracic compressor being positioned substantially adjacent to and lateral of the patient's thorax;

urging means for urging at least one of said thoracic compressors against the thorax, such that when a particular one of said thoracic compressors is actuated, said urging means causes said particular thoracic compressor to press against the thorax; and a compression controller for sequentially actuating and deactuating said first and said second thoracic compressors, wherein when said first thoracic compressor is inflated, the patient's thorax is compressed and pressure in the thorax increases, so that blood is driven away from the heart, and wherein when said second thoracic compressor is inflated, lateral force is applied to the patient's thorax, the patient's thorax is decompressed and pressure in the thorax decreases, so that blood is drawn toward the heart.

2. A device according to claim 1, wherein said urging means comprises an expansion limiting harness which at least partially surrounds at least one of the first and said second thoracic compressors and said patient.

3. A device according to claim 2, wherein said expansion limiting harness comprises:

a vest having at least one evacuable chamber; and a plurality of beads disposed in said evacuable chamber, wherein when said chamber is evacuated, said beads are compressed, and said vest stiffens.

4. A device according to claim 1, further comprising at least one set of electrical signal detection pads disposed in a location for detecting bodily electrical signals during operation of said device.

5. A device according to claim 1, further comprising at least a pair of defibrillation contact pads disposed in a location for performing cardiac defibrillation.

6. A device according to claim 1, wherein said device has an assist mode of operation wherein said device operates at least one of said first and said second thoracic compressors and said urging means in a manner suitable to assist the patient when the patient has impaired cardiac function, and a support mode of operation wherein said device operates at least one of said first and said second thoracic compressors and said urging means in a manner suitable to support the patient when the patient has no cardiac function.

7. A device according to claim 6, further comprising monitoring means for monitoring a condition of the patient and for selectively implementing said assist mode and said support mode.

8. A device according to claim 3, wherein at least one said thoracic compressor is affixed to said vest and further comprising means for attaching said affixed thoracic compressor to the patient, wherein when said thoracic compressor is deactuated, said thoracic compressor pulls on said patient's thorax.

9. A device according to claim 1, further comprising:

at least one abdominal bladder, said bladder suitably dimensioned and disposed to cover at least a portion of the abdomen of the patient, wherein said abdominal bladder is inflated to a predetermined volume or pressure or in timed sequence with the inflation of at least one of said thoracic compressors.

10. A device according to claim 1, further comprising ventilating means for ventilating the patient.

11. A device for compressing and decompressing a patient's thorax, the patient having a heart, comprising:

a first thoracic compressor and a first opposing surface, said first thoracic compressor and said first opposing surface being dimensioned and disposed so that when the patient is placed therebetween, said first thoracic compressor and said first opposing surface are respectively positioned anteriorly and posteriorly adjacent to the patient's thorax;

a second thoracic compressor and a second opposing surface, said second thoracic compressor and said second surface being dimensioned and disposed so that when the patient is placed therebetween, said second thoracic compressor and said second opposing surface are positioned adjacent to and laterally of the patient's thorax; and a compression controller for sequentially actuating and deactuating each of said first and said second thoracic compressors, wherein when said first thoracic compressor is actuated, the patient's thorax is compressed and pressure in the thorax increases, so that blood is driven away from the heart, and wherein when said second thoracic compressor is actuated, the patient's thorax is decompressed and pressure in the thorax decreases, so that blood is drawn toward the heart.

12. A device according to claim 11, further comprising at least one set of electrical signal detection pads disposed in a location for detecting bodily electrical signals during operation of said device.

13. A device according to claim 11, further comprising at least a pair of defibrillation contact pads disposed in a location for performing cardiac defibrillation.

14. A device according to claim 11, wherein said device has an assist mode of operation wherein said device operates at least one of said first and said second thoracic compressors in a manner suitable to assist the patient when the patient has impaired cardiac function, and a support mode of operation wherein said device operates at least one of said first and said second thoracic compressors and said urging means in a manner suitable to support the patient when the patient has no cardiac function.

15. A device according to claim 14, further comprising monitoring means for monitoring a condition of the patient and for selectively implementing said assist mode and said support mode.

16. A device according to claim 11, further comprising:

at least one abdominal bladder, said bladder suitably dimensioned and disposed to cover at least a portion of the abdomen of the patient, wherein said abdominal bladder is inflated in timed sequence to at least one of said thoracic compressors.

17. A device according to claim 11, further comprising ventilating means for ventilating the patient.

18. A device for compressing and decompressing a patient's thorax, the patient having a heart, comprising:

a first inflatable bladder and a first opposing surface, said first bladder and said first opposing surface being dimensioned and disposed so that when the patient is placed therebetween, said first bladder and said first opposing surface are respectively positioned across an anterior part and a posterior part of the patient's thorax;

a second inflatable bladder which is substantially adjacent to and lateral of the patient's thorax, and a second opposing surface, said second bladder and said second surface being dimensioned and disposed so that when the patient is placed therebetween, said second bladder and said second opposing surface are positioned across at least a part of the lateral regions of the patient's thorax; and an inflation controller for sequentially inflating and deflating said first and said second bladders, wherein said first bladder is inflated, the patient's thorax is compressed and pressure in the thorax increases, so that blood is driven away from the heart, and wherein when said second bladder is inflated, lateral force is applied to the patient's thorax and the patient's thorax is decompressed and pressure in the thorax decreases, so that blood is drawn toward the heart.

19. A device according to claim 18 further comprising:

urging means for urging at least one of said inflatable bladders against the thorax, such that when a particular one of said bladders is inflated, said urging means causes said particular bladder to press against the thorax.

20. A device according to claim 19, wherein said urging means comprises an expansion limiting harness which at least partially surrounds at least one of said bladders and the patient.

21. A device according to claim 20, wherein said expansion limiting harness comprises:

a vest having at least one evacuable chamber; and a plurality of beads disposed in said evacuable chamber, wherein said expansion limiting harness when said chamber is evacuated, said beads are compressed, and said vest rigidifies.

22. A device according to claim 18, further comprising at least one set of electrical signal detection pads disposed in a location for detecting bodily electrical signals during operation of said device.

23. A device according to claim 18, further comprising at least a pair of defibrillation contact pads disposed in a location for performing cardiac defibrillation.

24. A device according to claim 18, wherein said device has an assist mode of operation wherein said device operates at least one of said first and said second inflatable bladders in a manner suitable to assist the patient when the patient has impaired cardiac function, and a support mode of operation wherein said device operates at least one of said first and said second inflatable bladders in a manner suitable to support the patient when the patient has no cardiac function.

25. A device according to claim 24, further comprising monitoring means for monitoring a condition of the patient and for selectively implementing said assist mode and said support mode.

26. A device according to claim 21, wherein at least one of said bladders is affixed to said vest which can rigidify and further comprising means for attaching said bladder to the patient, wherein when said bladder which is affixed is deflated, said bladder pulls on the patient's thorax.

27. A device according to claim 18, further comprising:

at least one abdominal bladder, said bladder suitable dimensioned and disposed to cover at least a portion of the abdomen of the patient, wherein said abdominal bladder is inflated to a predetermined volume or pressure or in timed sequence to at least one of said thoracic bladders.

28. A device according to claim 18, further comprising ventilating means for ventilating the patient.

29. A device for compressing and decompressing a patient's thorax, the patient having a heart, comprising:

a first thoracic compressor;

a second thoracic compressor;

a third thoracic compressor acting in opposition to said second thoracic compressor, said first, said second, and said third thoracic compressors being dimensioned and disposed about the patient so that said first thoracic compressor is positioned across at least a part of an anterior region of the thorax, and said second and said third thoracic compressors are substantially adjacent to and lateral of the patient's thorax, and said second and third thoracic compressors are each positioned across at least a part of lateral regions of the thorax, and a compression controller for sequentially actuating and deactuating said first thoracic compressor and said second and third thoracic compressors, wherein when said first thoracic compressor is actuated, the patient's thorax is compressed and pressure in the thorax increases, so that blood is driven away from the heart, and wherein when said second and said third thoracic compressors are actuated, lateral force is applied to the patient's thorax, the patient's thorax is decompressed and pressure in the thorax decreases, so that blood is drawn toward the heart.

30. A device according to claim 29, wherein each of said first, second and said third thoracic compressors comprises an inflatable bladder, and further comprising:

at least one urging means for urging at least one of said inflatable bladders against the thorax, such that when a said bladder is inflated, said urging means causes at least said particular bladder to press against said thorax.

31. A device according to claim 30, wherein said urging means comprises an expansion limiting harness which at least partially surrounds at least one said bladder and the patient.

32. A device according to claim 31, wherein said expansion limiting harness comprises:

a vest having at least one evacuable chamber; and a plurality of beads disposed in said evacuable chamber, wherein when said chamber is evacuated, said beads are compressed, and said vest rigidifies.

33. A device according to claim 29, further comprising at least one set of electrical signal detection pads disposed in a location for detecting bodily electrical signals during operation of said device.

34. A device according to claim 29, further comprising at least a pair of defibrillation contact pads disposed in a location for performing cardiac defibrillation.

35. A device according to claim 29, wherein said device has an assist mode of operation wherein said device operates at least one of said first, said second and said third thoracic compressors in a manner suitable to assist the patient when the patient has impaired cardiac function, and a support mode of operation wherein said device operates at least one of said first, said second and said third thoracic compressors in a manner suitable to support the patient when the patient has no cardiac function.

36. A device according to claim 35, further comprising monitoring means for monitoring a condition of the patients and for selectively implementing said assist mode and said support mode.

37. A device according to claim 32, wherein at least one of said bladders is affixed to said vest which can rigidify and further comprising means for attaching said affixed bladder to the patient, wherein when said bladder which is affixed is deflated, said bladder pulls on the patient's thorax.

38. A device according to claim 29, further comprising:

at least one abdominal bladder, said bladder suitably dimensioned and disposed to cover at least a portion of the abdomen of the patient, wherein said abdominal bladder is inflated in relationship to at least one of said thoracic compressors.

39. A device according to claim 29, further comprising a fourth thoracic compressor, said fourth thoracic compressor being positioned across at least a part of a posterior region of the thorax.

40. A device according to claim 39, wherein said fourth thoracic compressor comprises an inflatable bladder.

41. A device according to claim 29, further comprising ventilating means for ventilating the patient.

42. A method of compressing and then decompressing a patient's thorax, the patient having a heart, comprising the steps of:

applying at least one of anterior pressure and posterior pressure to the thorax and compressing the thorax thereby increasing pressure in the thorax, so that blood is pushed from the heart;

relieving said at least one of anterior pressure and posterior pressure;

applying lateral pressure to the thorax and decompressing the thorax thereby decreasing pressure in the thorax, so that blood is drawn toward the heart;

relieving said lateral pressure; and regulating said steps of applying said at least one of anterior pressure and posterior pressure and applying lateral pressure to obtain alternate compression and decompression of the heart in the thorax at a rate which provides cardiac assistance.

43. A method according to claim 42, wherein said regulating is performed in response to detection of a heartbeat of the patient.

44. A method according to claim 42, further comprising the step of determining whether the patient requires cardiac support or cardiac assistance, and said regulating is selected accordingly.

45. A method according to claim 42, further comprising a step of ventilating the patient in timed sequence to said decompressing of said thorax.

* * * * *

UNITED STATES PATENT AND TRADEMARK OFFICE
CERTIFICATE OF CORRECTION

PATENT NO. : 5,490,820
DATED : February 13, 1996
INVENTOR(S) : ROBERT B. SCHOCK ET AL.    Page 1 of 3

It is certified that error appears in the above-identified patent and that said Letters Patent is hereby corrected as shown below:

On the title page: Item

AT [56] REFERENCES CITED

U.S. Patent Documents, insert
--3,745,998  7/1973  Rose  128/89R--.

Foreign Patent Documents, insert
--624118  1/1936  Germany
  2045451  2/1971  France--.

Other Publications, insert
--Halperin, Henry R. et al., "A Preliminary Study of Cardiopulmonary Resuscitation by Circumferential Compression of the Chest...", New England J. of Med., Vol. 329, No. 11, pp. 762-68 (9/9/93).
"CPR Vest Tested on Cardiac Arrest Victims", Adv. for Medical Laboratory Professionals" (10/18/93).--.

Other Publications, p. 2, under Halperin, Henry R. et al., "Dec. 1886" should read --Dec. 1986-- and under Cummins, Richard O. et al., "15," should read 15, 1985,--.

COLUMN 1

Line 56, "Pa." should read --Pat.--.

COLUMN 4

Line 16, "said" should read --the--.

UNITED STATES PATENT AND TRADEMARK OFFICE
CERTIFICATE OF CORRECTION

PATENT NO. : 5,490,820
DATED : February 13, 1996
INVENTOR(S) : ROBERT B. SCHOCK ET AL.

It is certified that error appears in the above-identified patent and that said Letters Patent is hereby corrected as shown below:

COLUMN 7

Line 57, "fluid tight" should read --fluid-tight--.

COLUMN 9

Line 25, "or" should read --or,--.
Line 32, "differently sized" should read --differently-sized---.

COLUMN 11

Line 18, "FIGS. 5A-5B," should read --5A-5E,--.
Line 21, "FIG. 5," should read --FIGS. 5A-5E,--.
Line 26, "FIGS. 5A-5B," should read --FIGS. 5A-5E,--.
Line 29, "dicrotic" should read --diacrotic--.

COLUMN 13

Line 11, "U-shaped" should read --⊔-shaped

COLUMN 14

Line 43, "the" should read --said--.
Line 44, "said" should read --the--.

COLUMN 15

Line 9, "said" (second occurrence) should read --the--.
Line 33, "surface" should read --opposing surface--.
Lines 60-61, delete "said urging means".

UNITED STATES PATENT AND TRADEMARK OFFICE
CERTIFICATE OF CORRECTION

PATENT NO. : 5,490,820
DATED : February 13, 1996
INVENTOR(S) : ROBERT B. SCHOCK ET AL.          Page 3 of 3

It is certified that error appears in the above-identified patent and that said Letters Patent is hereby corrected as shown below:

COLUMN 16

Line 25, "wherein" should read --wherein when--.
    Line 33, "claim 18" should read --claim 18,--.
    Line 48, delete, "said expansion limiting harness".

COLUMN 17

Line 9, "suitable" should read --suitably--.
    Line 45, "second" should read --said second--.
    Line 50, "said" (second occurrence) should read --the--.

COLUMN 18

Line 13, "patients" should read --patient--.
    Line 63, "said" should read --the--.

Signed and Sealed this

Twenty-third Day of July, 1996

Attest:

BRUCE LEHMAN

Attesting Officer          Commissioner of Patents and Trademarks